United States Patent [19]
Boone

[11] Patent Number: 6,017,321
[45] Date of Patent: *Jan. 25, 2000

[54] TAMPON REMINDER

[76] Inventor: Jeffrey S. Boone, 14309 Strawbridge Ct., Chesterfield, Mo. 63017-2831

[ * ] Notice: Under 35 U.S.C. 154(b), the term of this patent shall be extended for 110 days.

[21] Appl. No.: 08/655,736

[22] Filed: May 30, 1996

Related U.S. Application Data

[60] Provisional application No. 60/000,021, Jun. 8, 1995.

[51] Int. Cl.[7] ............................. A61F 13/20; A61F 13/15; A61B 17/06; A61B 19/02
[52] U.S. Cl. ............................. 604/11; 604/15; 604/540; 604/358; 604/904; 604/385.1; 40/107; 206/438; 206/828; 283/2; 283/900
[58] Field of Search ................................. 604/358, 385.1, 604/904, 11, 15; 40/107; 283/2, 117, 900; 206/823, 828, 438

[56] References Cited

U.S. PATENT DOCUMENTS

| | | | |
|---|---|---|---|
| 3,429,312 | 2/1969 | Stump | 604/18 |
| 3,948,275 | 4/1976 | Bossak . | |
| 4,332,551 | 6/1982 | Thompson | 604/904 |
| 4,941,688 | 7/1990 | Jones | 283/900 |
| 5,153,971 | 10/1992 | Van Iten . | |
| 5,350,371 | 9/1994 | Van Iten . | |
| 5,364,383 | 11/1994 | Hayes . | |

*Primary Examiner*—John G. Weiss
*Assistant Examiner*—K. M. Reichle

[57] ABSTRACT

A tampon reminder in the form of an adhesive sticker is disclosed. The user can remove the sticker and apply it to the users body, clothing, or a suitable object where it will serve to remind the user that the tampon is in use. The disclosed invention prevent tampons from being inadvertently left in place for an excessive time.

21 Claims, 6 Drawing Sheets

TAMPON REMINDER

This application is a continuation of prior application Ser. No. 60/000,021, filed Jun. 8, 1995, now abandoned.

BACKGROUND OF THE INVENTION

This invention relates to a reminder device to remind a woman that she is using a tampon.

Tampons are absorbent devices intended to be inserted into the vagina to adsorb menstrual fluids. Tampons are generally manufactured by cutting an absorbent material into a desired length, forming the length of material into a pledget, attaching a withdrawal string, and compressing the pledget. Typical of the art in tampons are U.S. Pat. No. 5,364,383 (Hayes; Tambrands; 1994), U.S. Pat. No. 5,153,971 (Van Iten; Kimberly-Clark; 1992), and U.S. Pat. No. 5,350,371 (Van Iten; Kimberly-Clark; 1994).

Great strides have been made in making tampons comfortable. However, an unfortunate consequence of comfortable tampons is that the user can easily forget that the tampon is in place. This can result in serious, even life-threating infections.

U.S. Pat. No. 3,948,275 (Bossak; 1976) discloses a deodorant device ("tag") attached to the free end of a tampon withdrawal string. Bossak mentions that the deodorant device may additionally perform the function of a warning that a tampon is in use. This device may be theoretically useful, but has limitations. In particular, the device may cause chafing or otherwise be uncomfortable to the user, particularly in sporting activities. Moreover, the tag may inadvertently become visible at the periphery of swimwear or similar clothing, causing embarrassment to the user.

Thus, it would be desirable to provide an improved tampon reminder device.

SUMMARY OF THE INVENTION

Briefly, the invention involves a tampon and an adhesive sticker used to remind a user of the tampon that the tampon is in use. The sticker can be affixed to the outside of a package for the tampon, inserted loose inside the package, affixed to the tampon itself, or affixed to a tampon applicator. The sticker can be included as a component of a kit including a tampon. The invention solves the problem of reminding users about tampons in use without the intrusiveness of the "tag" device of Bossak.

DETAILED DESCRIPTION OF THE INVENTION

In one embodiment the invention has a tampon, a package securing the tampon, and in close proximity to the package, an adhesive reminder sticker. By "in close proximity to the package" is meant, for example, that the adhesive reminder sticker may be affixed to the outside of the package, inserted loose inside the package (either in an inner single unit package or in an outer multi-unit package), affixed to the tampon itself, or affixed to a tampon applicator.

In another embodiment the invention is a kit of a tampon and an adhesive reminder sticker. The adhesive reminder sticker may, for example, be affixed to the body of the tampon directly, or may be affixed to the withdrawal string. In such embodiments it is anticipated that the sticker would be completely removable from the tampon.

The adhesives used in the adhesive reminder stickers of the invention may be any of several varieties. They may be of the type designed for removable application to clothing, such as is commonly used for name tags. Alternatively, they may be of the type designed for removable application to the human skin, such as is commonly used for bandages and other medical applications. Still further, the adhesive may be of the type used for application to file folders or mailing labels, etc.

In one embodiment the invention is a method of reminding that a tampon is in use in which the user removes an adhesive reminder sticker from a tampon, a tampon applicator, or a tampon package, and applies the adhesive reminder sticker to an object such as the user, the user's clothing, or another object.

Figure 1:
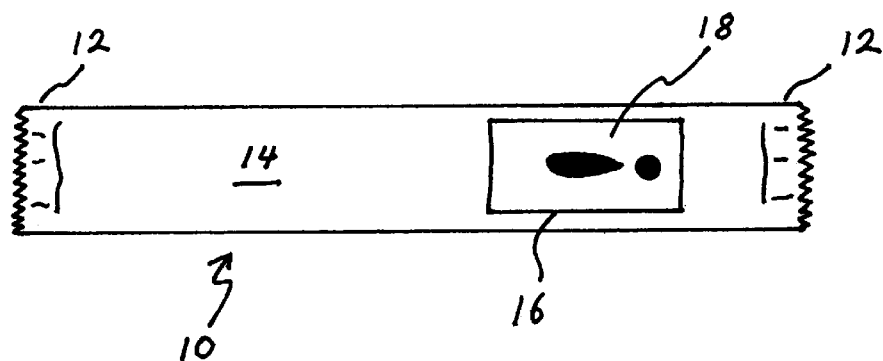
FIG. 1 is a view of a tampon package having an adhesive reminder sticker affixed thereto.

Referring to FIG. 1, a tampon package 10 has two sealed ends 12 and an outer surface 14. An adhesive label 16 bears a design 18, and is removably affixed to outer surface 14 of package 10. Adhesive reminder sticker 16 is intended to be removed from package 10 and affixed to an object such as the user's body or clothing, or to some other location such as a gym locker or bathroom mirror where it will serve the function of reminding the user that the tampon is in use.

Figure 2:
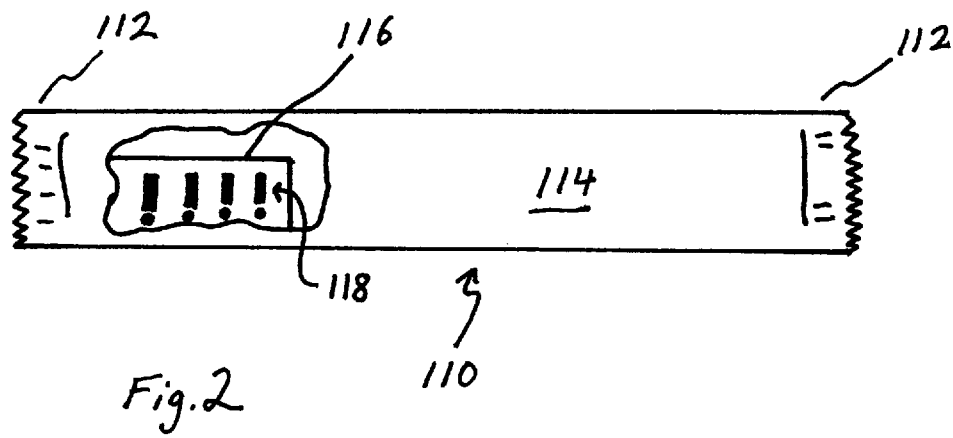
FIG. 2 is a partial cut-away view of a tampon package having an adhesive reminder sticker packaged loose inside the package.

FIG. 2 shows a tampon package 110 having sealed ends 112 and an outer surface 114. Through the partial cut-away can be seen adhesive reminder sticker 116 bearing a design 118, loose in package 110.

Figure 3:
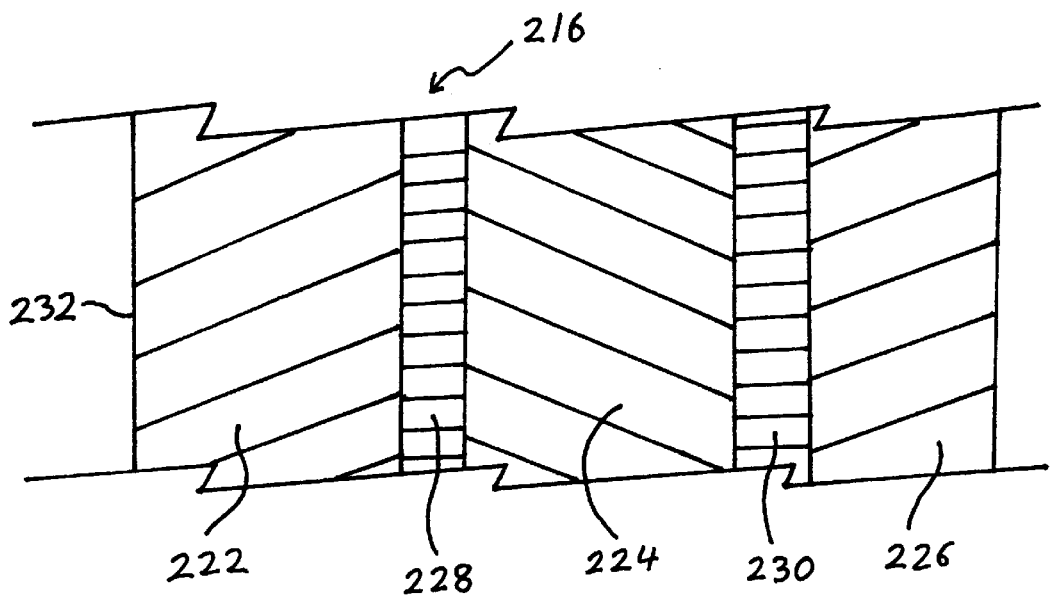
FIG. 3 is a cross-sectional view of a composite adhesive reminder sticker.

Referring to FIG. 3 (not to scale), a composite adhesive reminder sticker 216 has a removable slip 222 with a visible surface 232 bearing a design (not shown), and backing slip 224. A permanent adhesive layer 230 secures backing slip 224 to a material 226 which may be, for example, a tampon package or a tampon applicator. A releasable adhesive layer 228 secures removable slip 222 to backing slip 224. When removable slip 222 is removed, releasable adhesive layer 228 remains affixed to removable slip 222 and releases from backing slip 224, so that removable slip 222 may be adhesively affixed to another object.

Figure 4:
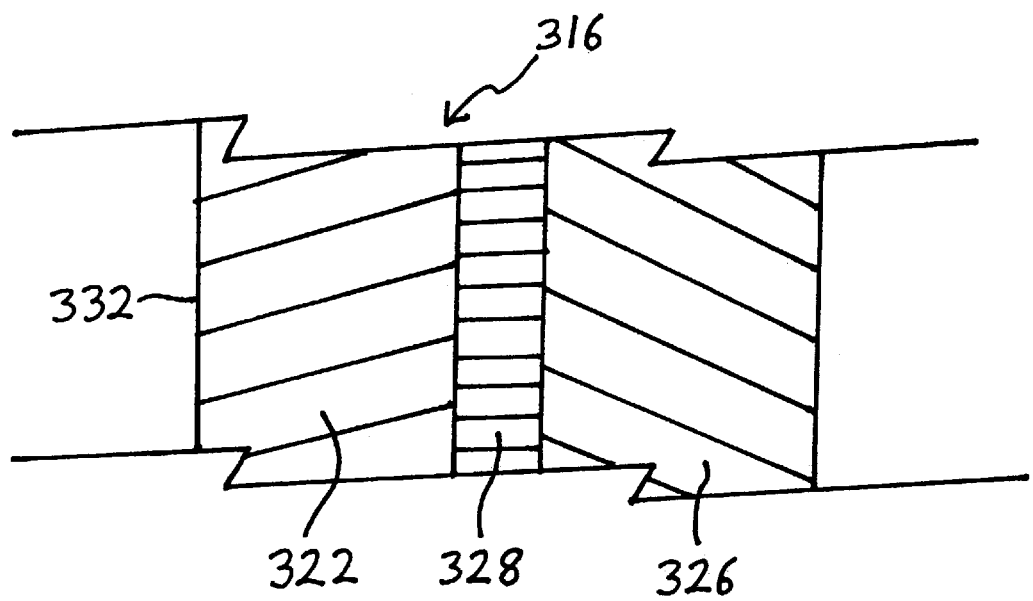
FIG. 4 is a cross-sectional view of a completely removable adhesive reminder sticker.

Referring to FIG. 4 (not to scale), a completely removable adhesive reminder sticker 316 has a removable slip 322 with a visible surface 332 bearing a design (not shown). A releasable adhesive layer 328 secures removable slip 322 to a material 326 which may be, for example, a tampon package or a tampon applicator. When removable slip 322 is removed, releasable adhesive layer 328 remains affixed to removable slip 322 and releases from material 326, so that removable slip 322 may be adhesively affixed to another object. This leaves material 326 free of any remnant of completely removable adhesive reminder sticker 316.

Figure 5:
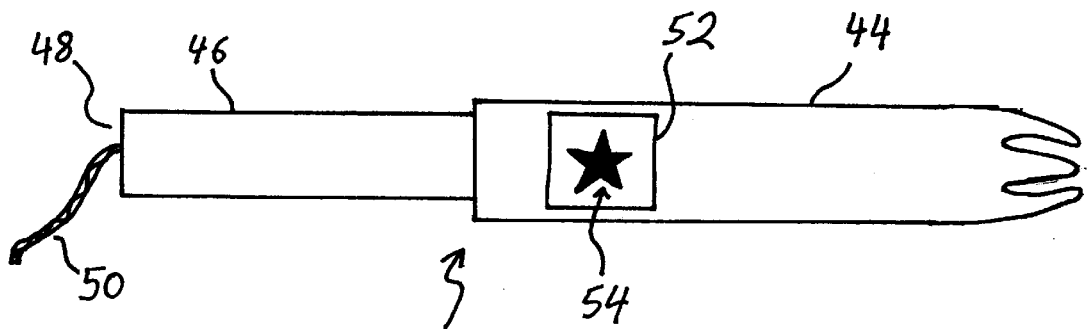
FIG. 5 is a view of a tampon applicator bearing an adhesive reminder sticker.

FIG. 5 shows a tampon applicator 42 having a barrel portion 44, and a plunger portion 46 which has a distal end 48. A string 50 is shown exiting from the distal end 48 of plunger portion 46. The string 50 is attached to a tampon (not shown) inside barrel portion 44. An adhesive reminder sticker 52, bearing a design 54, is affixed to barrel portion 44. The adhesive reminder sticker in this embodiment is intended to be of the completely removable type as shown in FIG. 4.

In other embodiments the adhesive reminder sticker 52 could be placed on the plunger portion 46 or on the distal end 48 of plunger portion 46. In these embodiments adhesive reminder sticker 52 could be either of the composite type as shown in FIG. 3, or of the completely removable type as shown in FIG. 4.

Figure 6:
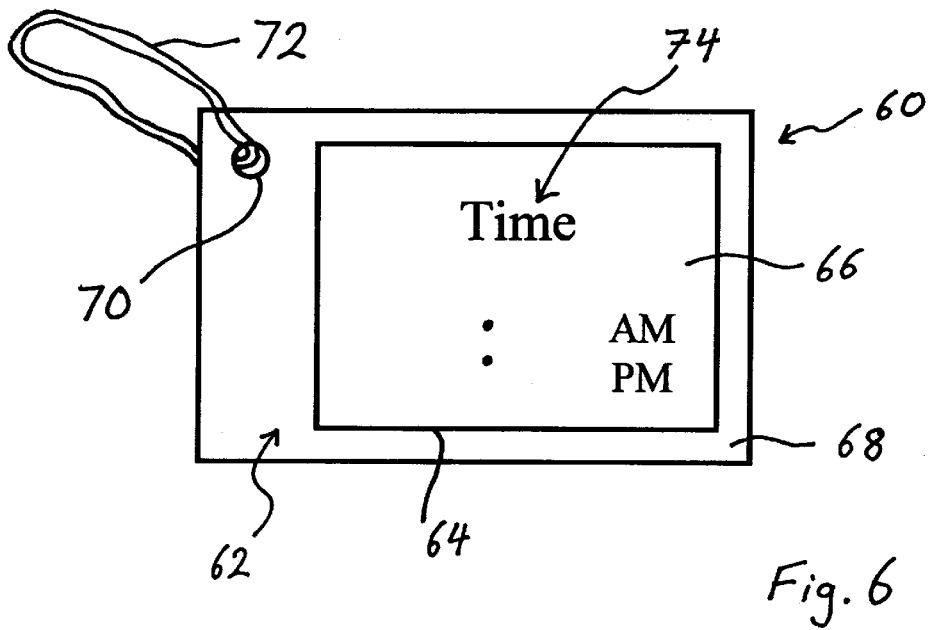
FIG. 6 is a view of an adhesive reminder sticker having an elastic attachment.

FIG. 6 shows an adhesive reminder sticker 60 in the form of a composite label, but without the permanent adhesive layer 230 shown in FIG. 3. Sticker 60 includes a removable slip 62 divided by a die cut 64 into a removable portion 66, and a remaining portion 68. Removable slip 62 is atop a backing slip (not shown) and is secured thereto by an removable adhesive layer (not shown). A hole 70 has been punched in adhesive reminder sticker 60 to receive an elastic attachment cord 72. Elastic attachment cord 72 is intended to be secured around the tampon, applicator, or package (not shown) by the tampon manufacturer. In this embodiment removable portion 66 bears a design 74 which includes a space for the user to record the time the tampon was inserted or the time the user should remove the tampon.

Figure 7:
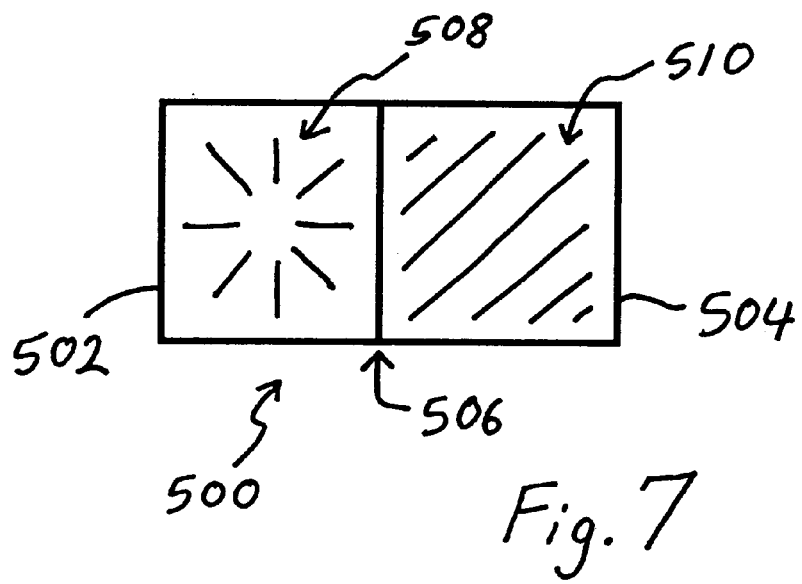
FIG. 7 is a view of an adhesive reminder sticker having two separable parts.

FIG. 7 shows an adhesive reminder sticker 500 having two separable parts 502 and 504, divided by a die cut 506. Separable part 502 bears a design 508 and separable part 504 bears a design 510. In this embodiment designs 508 and 510 are different to allow the user to pick the design that is most suitable. Some users may choose an adhesive reminder sticker separable part which is large and of a bright color to serve as a bold reminder. Other users may choose an adhesive reminder sticker separable part which is small and of a very light color to avoid having it show through light clothing.

Figure 8:
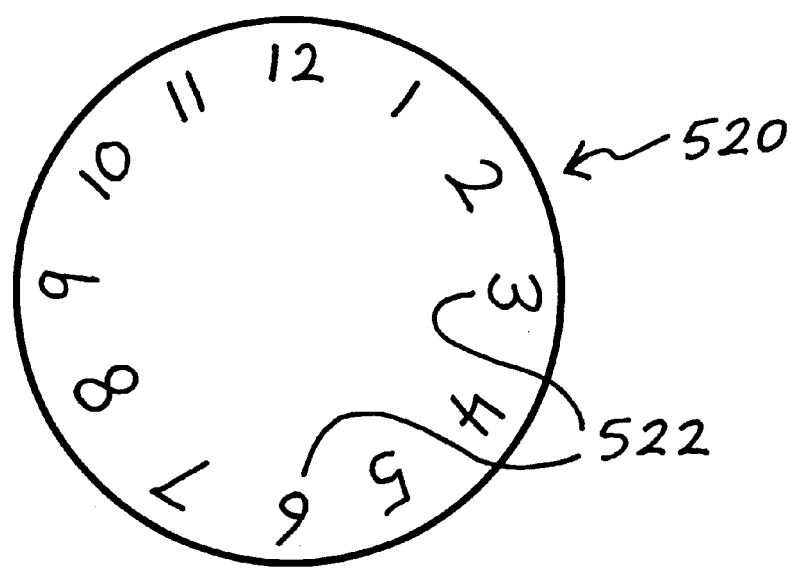
FIG. 8 is a view of an adhesive reminder sticker which is rotatable according to a time of day.

FIG. 8 shows an adhesive reminder sticker 520 which bears a design featuring numbers 522 which correspond to a time of day. The user can apply the adhesive reminder sticker so that the time the tampon was inserted or the time the tampon should be removed is oriented at the top.

Figure 9:
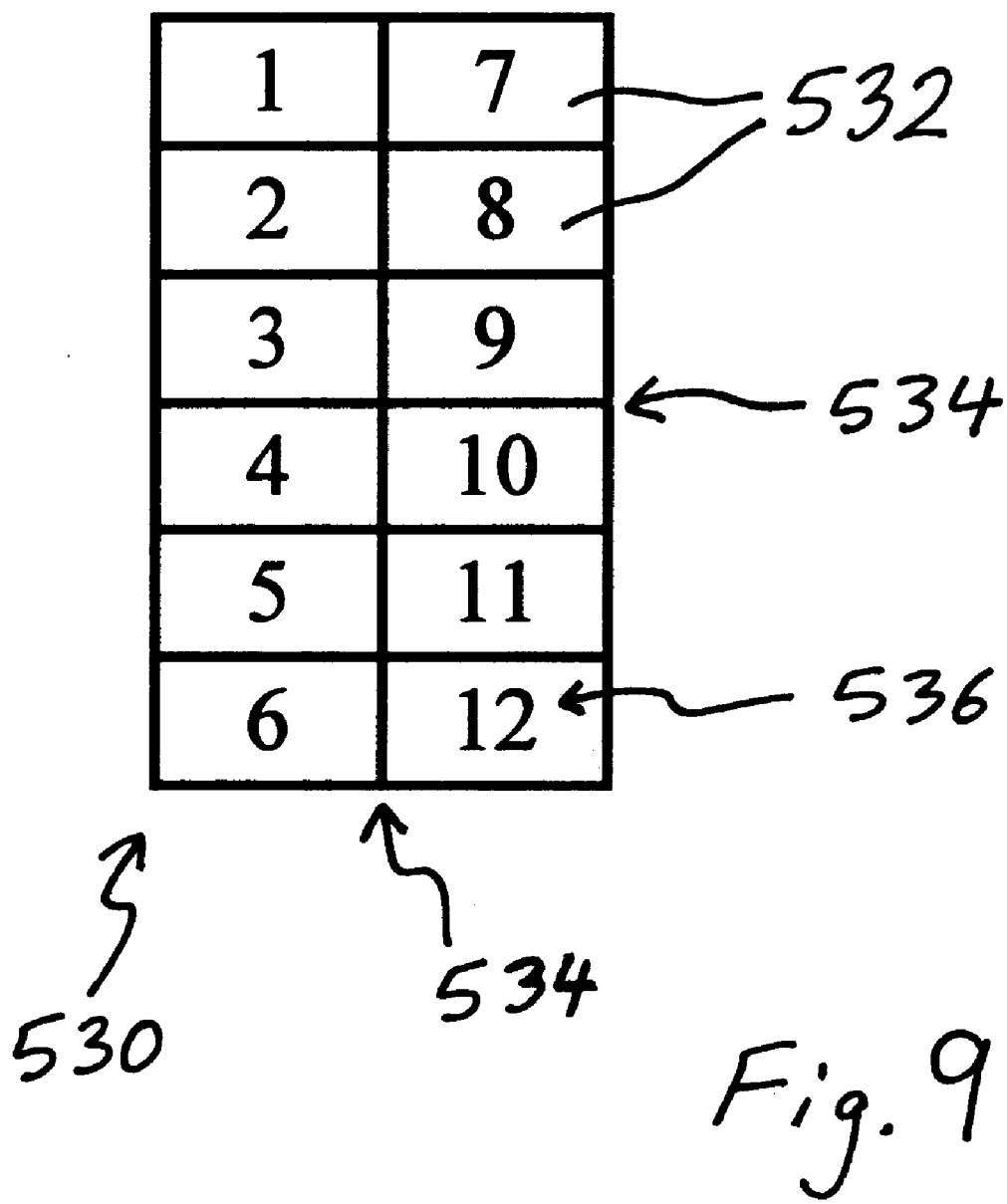
FIG. 9 is a view of an adhesive reminder sticker having separable parts which correspond to a time of day.

FIG. 9 shows an adhesive reminder sticker 530 having numerous separable parts 532 separated by die cuts 534. Each separable part 532 bears a different design 536 which correspond to a time of day. The user can choose the separable part 532 which corresponds to the time the tampon was inserted or the time the tampon should be removed.

Figure 10:
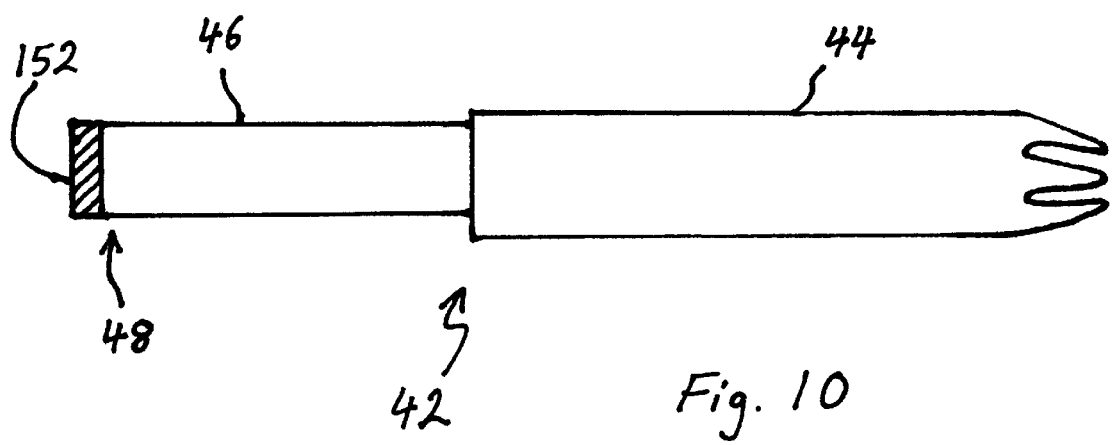
FIG. 10 is a view of a tampon applicator bearing an adhesive reminder sticker at the terminal end of the plunger portion.

FIG. 10 shows a tampon applicator 42 having a barrel portion 44 and a plunger portion 46 which has a distal end 48. An adhesive reminder sticker 152 (not to scale) is affixed to the distal end 48 of plunger portion 46, sealing it.

It will be understood that the adhesive reminder sticker can be in many forms and still be with the scope of the invention.

It will be appreciated that the adhesive reminder stickers of the invention are economical to manufacture and easy for the consumer to use.

What is claimed is:

1. A tampon device comprising
   (a) a tampon;
   (b) a package securing said tampon; and
   (c) an adhesive reminder sticker affixed to the outside of said package, inserted loose inside said package, or affixed to the tampon itself.

2. The tampon device of claim 1 wherein said package has an outside and said adhesive reminder sticker is affixed to the outside of said package.

3. The tampon device of claim 1 wherein said adhesive reminder sticker is inserted loose inside said package.

4. The tampon device of claim 1 wherein said adhesive reminder sticker includes an adhesive particularly suited for application to human skin.

5. The tampon device of claim 1 wherein said adhesive reminder sticker includes an adhesive particularly suited for application to clothing.

6. A tampon applicator device comprising
   (a) a tampon applicator; and
   (b) an adhesive reminder sticker affixed to said applicator.

7. The tampon device of claim 6 wherein said applicator includes a plunger portion and a barrel portion, and said adhesive reminder sticker is completely removably affixed to the barrel portion.

8. The tampon device of claim 6 wherein said applicator includes a plunger portion and a barrel portion, and said adhesive reminder sticker is affixed to the plunger portion.

9. The tampon device of claim 8 wherein the plunger portion of said applicator has a terminal end and said adhesive reminder sticker is affixed to the terminal end of the plunger portion.

10. The tampon device of claim 9 wherein said adhesive reminder sticker seals the terminal end of the plunger portion.

11. The tampon device of claim 6 wherein said adhesive reminder sticker is affixed to said applicator by an elastic band.

12. The tampon applicator device of claim 6 wherein said adhesive reminder sticker includes an adhesive particularly suited for application to human skin.

13. The tampon applicator device of claim 6 wherein said adhesive reminder sticker includes an adhesive particularly suited for application to clothing.

14. A tampon device kit comprising
   (a) a tampon; and
   (b) an adhesive reminder sticker.

15. The tampon device kit of claim 14 wherein said adhesive reminder sticker is completely removably affixed to said tampon.

16. The tampon device kit of claim 14 wherein said tampon includes a withdrawal string element and said adhesive reminder sticker is completely removably affixed to the withdrawal string.

17. The tampon applicator kit of claim 14 wherein said adhesive reminder sticker includes an adhesive particularly suited for application to human skin.

18. The tampon device kit of claim 14 wherein said adhesive reminder sticker includes an adhesive particularly suited for application to clothing.

19. A method of reminding a tampon user that a tampon has been used, comprising
   (a) removing an adhesive reminder sticker from a tampon, tampon applicator, or tampon package; and
   (b) applying said adhesive reminder sticker to an object.

20. The method of claim 19 wherein said object is the user's body.

21. The method of claim 19 wherein said object is the user's clothing.

* * * * *